United States Patent [19]

Kleinschmit et al.

[11] 4,180,684

[45] Dec. 25, 1979

[54] PROCESS FOR THE PRODUCTION OF 4,4-ISOPROPYLIDENE-BIS'(2,6-DIBROMO-PHENOL)

[75] Inventors: Peter Kleinschmit; Eberhard Walter, both of Hanau; Helmut Mechler, Hofheim; Günter Theis, Hanau; Brigitte Meiners, Kahl, all of Fed. Rep. of Germany

[73] Assignee: Deutsche Gold- und Silber-Scheideanstalt vormals Roessler, Frankfurt, Fed. Rep. of Germany

[21] Appl. No.: 759,548

[22] Filed: Jan. 14, 1977

[30] Foreign Application Priority Data

Jan. 17, 1976 [DE] Fed. Rep. of Germany ....... 2601681

[51] Int. Cl.$^2$ .............................................. C07C 37/00
[52] U.S. Cl. ..................................... 568/726; 568/725
[58] Field of Search .................... 260/619 A; 568/726

[56] References Cited

U.S. PATENT DOCUMENTS

| | | | |
|---|---|---|---|
| 3,546,302 | 12/1970 | Asadonan et al. | 260/619 A |
| 3,929,907 | 12/1975 | Janzon et al. | 260/619 A |

FOREIGN PATENT DOCUMENTS

| | | |
|---|---|---|
| 1768444 | 7/1971 | Fed. Rep. of Germany . |
| 2274586 | 1/1976 | France . |

*Primary Examiner*—Norman Morgenstern
*Attorney, Agent, or Firm*—Cushman, Darby & Cushman

[57] ABSTRACT

4,4'-isopropylidene-bis(2,6-dibromophenol) is produced by reacting 4,4'-isopropylidene diphenol with hydrogen bromide or a mixture of hydrogen bromide with up to an equimolar amount of free bromine in admixture with hydrogen peroxide and in the presence of water and an inert organic liquid.

14 Claims, No Drawings

PROCESS FOR THE PRODUCTION OF 4,4-ISOPROPYLIDENE-BIS'(2,6-DIBROMO-PHENOL)

BACKGROUND OF THE INVENTION

The invention is directed to a process for the production of pure 4,4'-isopropylidene-bis(2,6-dibromophenol) by reaction of 4,4'-isopropylidene diphenol with a brominating agent in the presence of water and an inert organic liquid. 4,4'-isopropylidene-bis(2,6-dibromophenol) is employed as a flameproofing agent. For example, it is admixed with synthetic resins for this purpose. In order that the synthetic resin is not colored in an undesirable way, it is necessary to use a correspondingly pure, non-coloring 4,4'-isopropylidene-bis (2,6-dibromophenol).

It is known to produce 4,4'-isopropylidene-bis(2,6-dibromophenol) by brominating 4,4'-isopropylidene diphenol. As the brominating agent there is used bromine. The reaction is carried out in the presence of two liquid phases, namely, water and an organic liquid which is only slightly miscible with water. The 4,4'-isopropylidene-bis(2,6-dibromophenol) formed is recovered from the reaction mixture by filtration. The mother liquor resulting as the filtrate and which contains hydrogen bromide is used as the reaction medium for a subsequent charge (Jenkner, German Pat. No. 1,768,444).

It is also known to carry out the bromination with the addition of an oxidizing agent. As the oxidizing agent, there is primarily employed chlorine, alkali chlorate or alkali bromate, see Asadorian U.S. Pat. No. 3,546,302 or hydrogen peroxide, see German Offenlegungsschrift No. 2,227,439 and related Janzon U.S. Pat. No. 3,929,907. The entire disclosures of the Asadorian and Janzon U.S. patents are hereby incorporated by reference and relied upon.

A disadvantage of the known processes is that discoloring byproducts are formed to a considerable extent. The 4,4'-isopropylidene-bis(2,6-dibromophenol) separating from the reaction mixture contains this type of impurities in undesired amounts. Particularly if the motor liquor is reused as the reaction medium the 4,4'-isopropylidene-bis (2,6-dibromophenol) is obtained in highly impure form. Of course, it is possible to purify the material from discolouring byproducts, but thereby the yield is reduced considerably.

SUMMARY OF THE INVENTION

There has now been developed a process for the production of pure 4,4'-isopropylidene-bis(2,6-dibromophenol) by reaction of 4,4-isopropylidene diphenol with a bromination agent in the presence of water and an inert organic liquid that is characterized by employing as the brominating agent hydrogen bromide alone or hydrogen bromide which contains per mole of the hydrogen bromide up to about one mole of free bromine, in admixture with hydrogen peroxide. Surprisingly, in this process color causing impurities are formed only to a very small extent. The 4,4'-isopropylidene-bis(2,6-dibromophenol) separates from the reaction mixture directly in very high purity. Also, if there is employed a mother liquor which has already served several times as reaction medium there is recovered an outstandingly pure 4,4'-isopropylidene-bis(2,6-dibromophenol) which is directly usable for all usual applications as a flameproofing agent. The yield of pure substance obtained in the process of the invention is at least as high as the yield of impure substance obtained in the known processes.

To carry out the process of the invention there is used as a brominating agent hydrogen bromide in admixture with hydrogen peroxide. Instead of hydrogen bromide alone there can be used a mixture of free bromine with hydrogen bromide which per mole of hydrogen bromide contains up to about one mole of free bromine. The reaction of the 4,4'-isopropylidene diphenol takes place in the presence of water and an organic liquid which has a limited miscibility with water, so that two liquid phases are present. As organic liquids there can be employed organic materials which are liquids under the conditions of reaction and also are inert under such conditions. Particularly suitable are halogenated aliphatic or aromatic hydrocarbons. Preferably there is used tetrachloroethylene or chlorobenzene. Additional examples of suitable solvents are carbon tetrachloride, ethylene dibromide, ethylene dichloride, chloroform, fluorobenzene, 1,1,2-trichloroethane, 1,1,1-trichloroethane, propylene dichloride, dibromotetrafluoroethane, trichlorotrifluoroethane, propyl bromide, tetrachlorodifluoroethane, butyl chloride, amyl chloride and hexyl chloride. Also there can be used aliphatic and aromatic hydrocarbons, e.g., benzene, toluene, o-xylene, m-xylene, p-xylene, alkanes, e.g., n-pentane, n-hexane, n-octane, n-decane, gasoline and petroleum ether.

The water and the organic liquid can be present as such or can be introduced entirely or partially by solutions of the starting materials in water and/or in the organic liquid. The proportions of water to organic liquid which are used depend essentially on the type of organic liquid. Generally it is advantageous to so choose the amounts that for one part by volume of water phase there will be about 1 to 20, especially 1 to 10, parts by volume of the organic phase formed from the organic liquid.

For each mole of 4,4'-isopropylidene diphenol according to stoichiometry there are needed 4 gram atoms of bromine. It is suitable to use not substantially less brominating agent than corresponds to this stoichiometric ratio. Generally, it is advantageous to employ the brominating agent in excess. Advantageously there are used per mole of 4,4'-isopropylidene diphenol about 4.0 to 4.2 gram atoms, especially 4.0 to 4.1 gram atoms of bromine (whether the bromine is present all as hydrogen bromide or partially as free bromine). As stated previously, according to the invention hydrogen bromide is added alone or there is added hydrogen bromide containing free bromine. Since both the hydrogen bromide added as well as the hydrogen bromide formed during bromination are intended to be used for the bromination, according to stoichiometry for each mole of hydrogen bromide added there is needed one mole of hydrogen peroxide and for each mole of free bromine added there is likewise needed one mole of hydrogen peroxide. Accordingly, there is suitably used per mole of hydrogen bromide added or free bromine added at least about 1.0 mole, preferably about 1.0 to 1.2 moles, especially 1.0 to 1.1 moles of hydrogen peroxide.

The hydrogen bromide or mixture of hydrogen bromide and bromine is suitably added as an aqueous solution. Although any dilute solution can be used it is advantageous to use solutions containing about 30 to 65 weight percent of hydrogen bromide. It is also possible, for example, initially to start with water and to add the hydrogen bromide, and in a given case the bromine also, in gaseous form. The hydrogen peroxide likewise is suitably added as an aqueous solution. The solution can be of any concentration. However, there are preferred solutions containing 30 to 70 weight percent of hydrogen peroxide. It can be advantageous to use the hydrogen peroxide as a solution in dilute mineral acids, for example in 1 to 5 weight percent sulfuric acid or phosphoric acid.

It is advantageous to add the hydrogen peroxide and the hydrogen bromide or the mixture of hydrogen bromide and bromine in such manner that in the reaction mixture there is always present somewhat more hydrogen peroxide than that which corresponds stoichiometrically to the amount of bromine present. Preferably the excess of hydrogen peroxide to hydrogen bromide or mixture of hydrogen bromide and bromine should amount to 2 to 10 mole percent.

The reaction generally takes place at temperatures between about 0° and 100° C. Preferably the temperature range is between 10° and 90° C. Although the pressure can be selected at random in a wide range, it is advantageous in order to use a simple apparatus not to deviate substantially from normal pressure. On account of the volatility of the hydrogen bromide and the bromine it can be suitable to operate at an elevated pressure corresponding to the temperature.

In order to recover the 4,4'-isopropylidene-bis (2,6-dibromophenol) from the reaction mixture it is generally suitable to separate the phases, to wash the organic phase with hot water until it is neutral and then to cool it, followed by filtering off and drying the 4,4'-isopropylidene-bis(2,6-dibromophenol) precipitated.

The filtrate remaining can be used directly as the reaction medium for a subsequent preparation.

An especially advantageous method of operation is as follows:

There is present an organic liquid, preferably tetrachloroethylene or chlorobenzene, saturated with 4,4'-isopropylidene-bis(2,6-dibromophenol). To this organic phase there is added, in a given case gradually in portions, 4,4'-isopropylidene diphenol as a solid and hydrogen peroxide as an aqueous sulfuric acid or phosphoric acid solution. There is fed into this mixture under strong stirring, in a given case gradually in portions, the hydrogen bromide or the bromine-hydrogen bromide mixture as an aqueous solution. This feeding takes place in such manner that there is always present hydrogen peroxide in excess in relation to the hydrogen bromide or hydrogen bromide-bromine. Furthermore, the concentrations are so adapted to the reaction temperature that except towards the end of the reaction non-dissolved 4,4'-isopropylidene diphenol is present. The organic phase remaining after the separation of the 4,4'-isopropylidene-bis(2,6-dibromophenol) which is saturated with 4,4'-isopropylidene-bis(2,6-dibromophenol), is recycled and is used as reaction medium for a subsequent batch.

The process can comprise, consist essentially of or consist of the steps set forth and using the materials described.

In the specification, claims and the following examples, unless otherwise indicated, all parts and percents are by weight.

EXAMPLE 1

There were present 3 liters of chlorobenzene which was saturated with 4,4'-isopropylidene-bis(2,6-dibromophenol). There were introduced into this solution 0.5 kg of 4,4'-isopropylidene diphenol as a solid as well as 0.63 kg of a 50 percent aqueous hydrogen peroxide solution and 0.04 kg of 50 percent aqueous sulfuric acid. The materials were intensively mixed with each other. Then in the course of 2 hours there were added 1.83 kg of 40 percent aqueous hydrobromic acid. During this time and for a further half hour the mixture was held at temperatures not over 30° C. Subsequently, the temperature was increased to 80° C. in the course of half an hour.

The organic phase was separated from the water phase while the temperature was held at 80° C. and subsequently washed with water at the same temperature until it was neutral. Then with stirring it was slowly cooled to 20° C. The precipitating 4,4'-isopropylidene-bis(2,6-dibromophenol) was separated from the mother liquor by centrifugation and then dried. There were recovered 1.16 kg of 4,4'-isopropylidene-bis (2,6-dibromophenol) corresponding to a yield of 98% based on the 4,4'-isopropylidene diphenol added. The 4,4'-isopropylidene-bis(2,6-dibromophenol) had a melting point of 180° to 181° C. and a bromine content of 58.6% compared to a theoretical of 58.8%.

The mother liquor remaining after the centrifugation which was saturated with 4,4'-isopropylidene-bis(2,6-dibromophenol) was brought to a volume of 3 liters by addition of chlorobenzene and used as the reaction medium for a subsequent batch. After ten reuses of the mother liquor the then recovered 4,4'-isopropylidene-bis(2,6-dibromophenol) was tested as to its color. The Hazen color number was determined on a 50 percent solution of the product in acetone according to DIN 53409 (German Industrial Standard 53409). It corresponded to a standard solution of 35 mg Pt.

EXAMPLE 2

The procedure was the same as in Example 1 except that there were used 0.42 kg of the 50 percent aqueous hydrogen peroxide solution and there were added 1.83 kg of aqueous hydrobromic acid which besides 0.24 kg of hydrogen bromide contained 0.49 kg of free bromide. The yield of 4.4'-isopropylidene-bis(2,6-dibromophenol) amounted to 1.16 kg, corresponding to 98% based on the 4,4'-isopropylidene diphenol added. The 4,4'-isopropylidene-bis(2,6-dibromophenol) had a melting point of 181° to 182° C. and a bromine content of 58.7% compared to a theoretical of 58.8%. After ten reuses of the mother liquor the product recovered showed a Hazen color number which corresponded to a standard solution of 35 mg Pt.

EXAMPLE 3

The process was the same as in Example 1 but there were present 4 liters of tetrachloroethylene (rather than the chlorobenzene) which was saturated at 20° C. with 4,4'-isopropylidene-bis(2,6-dibromophenol). The temperature was first held at 30° C. and subsequently increased to 90° C. The phase separation and water washing took place at 90° C. There were recovered 1.17 kg of 4,4'-isopropylidene-bis(2,6-dibromophenol), corresponding to a yield of 98% based on the 4,4'-isopropylidene diphenol employed. The 4,4'-isopropylidene-bis(2,6dibromophenol) had a melting point of 180° to 181° C. and a bromine content of 58.7% compared to a theoretical of 58.8%. After ten reuses of the mother liquor the product recovered had a Hazen color number which corresponded to that of a standard solution of 30 mg Pt.

COMPARISON EXAMPLE

The procedure was the same as in Example 1 except there were used 0.32 kg of 50 percent aqueous hydrogen peroxide. In place of hydrogen bromide there was added elemental bromine in an amount of 0.72 kg. After two reuses of the mother liquor the product recovered had a Hazen color number which corresponded to a standard solution of 30 mg Pt. After three reuses of the mother liquor the product was clearly colored yellow so that it was not suited, for example, for employment as a flameproofing agent.

What is claimed is:

1. A process for the production of pure 4,4'-isopropylidene-bis (2,6-dipromophenol) comprising reacting 4,4'-isopropylidene diphenol with a brominating agent selected from the group consisting of (1) hydrogen bromide and (2) hydrogen bromide containing up to 1 mole of free bromine per mole of hydrogen bromide and at least about 1.0 mole of hydrogen peroxide for each mole total of hydrogen bromide and free bromine in the presence of water and an inert ogranic solvent which has limited miscibility with water so that two liquid phases are present, one phase being a water phase and the other an organic solvent phase, separating the water phase from the organic solvent phase, precipitating 4,4'-isopropylidene-bis (2,6-dibromophenol) from the organic phase to leave a mother liquor and recycling the mother liquor for use as water immiscible solvent in making another batch of 4,4'-isopropylidene-bis (2,6-dibromophenol).

2. A process according to claim 1 wherein for each mole of 4,4'-isopropylidene diphenol there is employed about 4.0 to 4.2 gram atoms of bromine in the brominating agent.

3. A process according to claim 2 wherein for each mole total of hydrogen bromide and free bromine there is employed about 1.0 to 1.2 moles of hydrogen peroxide.

4. A process according to claim 3 wherein the reaction is carried out at 10 to 90° C.

5. A process according to claim 2 wherein the solvent is a chlorinated aliphatic hydrocarbon or chlorinated aromatic hydrocarbon.

6. A process according to claim 5 wherein the solvent is tetrachloroethylene or chlorobenzene.

7. A process according to claim 2 wherein the brominating agent is employed in aqueous mineral acid.

8. A process according to claim 7 wherein the mineral acid is sulfuric acid or phosphoric acid.

9. A process according to claim 2 wherein the brominating agent is hydrogen bromide free of elemental bromine.

10. A process according to claim 2 wherein the brominating agent is hydrogen bromide containing free bromine.

11. A process according to claim 1 wherein the solvent is an aliphatic hydrocarbon, aromatic hydrocarbon, a chlorinated aliphatic hydrocarbon or chlorinated aromatic hydrocarbon.

12. A process according to claim 11 wherein the solvent is a chlorinated aliphatic hydrocarbon or chlorinated aromatic hydrocarbon.

13. A process according to claim 12 wherein for each mole of 4,4'-isopropylidene diphenol, there is employed about 4.0 to 4.2 gram atoms of bromine in the brominating agent.

14. A process according to claim 1 wherein the recycling is carried out 10 times.

* * * * *